(12) United States Patent
Adiga et al.

(10) Patent No.: US 8,790,575 B1
(45) Date of Patent: Jul. 29, 2014

(54) METHOD AND APPARATUS FOR REMOVING RESIDUAL BIOCIDE FROM A DECONTAMINATION AREA

(71) Applicants: Kayyani C. Adiga, Macon, GA (US); Rajani Adiga, Macon, GA (US); Robert F. Hatcher, Jr., Macon, GA (US)

(72) Inventors: Kayyani C. Adiga, Macon, GA (US); Rajani Adiga, Macon, GA (US); Robert F. Hatcher, Jr., Macon, GA (US)

(73) Assignee: Nano Mist Systems, LLC, Macon, GA (US)

( * ) Notice: Subject to any disclaimer, the term of this patent is extended or adjusted under 35 U.S.C. 154(b) by 0 days.

(21) Appl. No.: 13/921,142

(22) Filed: Jun. 18, 2013

(51) Int. Cl.
 *A61L 9/00* (2006.01)
(52) U.S. Cl.
 USPC .................. 422/4; 422/5; 422/120; 422/122; 422/123

(58) Field of Classification Search
 USPC .................. 422/4, 5, 120, 122, 123
 See application file for complete search history.

(56) References Cited

U.S. PATENT DOCUMENTS

| | | | |
|---|---|---|---|
| 2009/0041617 A1* | 2/2009 | Lee | 422/4 |
| 2010/0178196 A1* | 7/2010 | Garner | 422/4 |
| 2011/0229369 A1* | 9/2011 | Carson et al. | 422/4 |
| 2012/0087827 A1* | 4/2012 | Temple | 422/4 |

* cited by examiner

*Primary Examiner* — Timothy Vanoy
(74) *Attorney, Agent, or Firm* — Jean L. Simunic

(57) ABSTRACT

An apparatus and method are disclosed for improving the efficiency of an aerator which is used for removing residual biocide used for decontamination, sterilization, sanitation, or disinfection processes. The apparatus comprises an aerator assembly that produces an optimum air flow region and a high surface area catalyst panel. The method comprises utilizing the apparatus with optimizing gas flow rates, residence time of the contaminated gas within the catalyst panel, air flow pattern, air transport rate, cleaned air discharge pattern, and the nature and configuration of the catalyst.

29 Claims, 6 Drawing Sheets

METHOD AND APPARATUS FOR REMOVING RESIDUAL BIOCIDE FROM A DECONTAMINATION AREA

CROSS-REFERENCE TO PRIOR APPLICATIONS

The present application does not claim priority to any previously filed U.S. patent applications.

BACKGROUND

The present invention relates to a system and a method for reducing residual biocide vapor following an area decontamination process to a level safe for reentry into the area. More specifically, this invention relates to a method and apparatus for rapidly reducing the hydrogen peroxide (HP) vapor concentration from a volume in an area decontamination process. Rapid removal of the residual HP minimizes the downtime of the facility thereby increasing productivity. The present inventive apparatus comprises an aerator having a high surface area catalyst panel. Rapid HP vapor concentration reduction is achieved by optimizing air flow pattern, air transport rate, cleaned air discharge pattern, and the nature and configuration of the catalyst. The result is a 3- to 4-fold efficiency increase as compared to the prior art.

There is a need for decontaminating various enclosed areas such as hotel rooms, hospitals, airports, crew ships, clean rooms, laboratories, and many public and private facilities. These areas can be decontaminated by filling the area with a vaporized sterilizing agent. Hydrogen peroxide (HP) is commonly used in the decontamination process: a mist or vapor of hydrogen peroxide in water floods the area to be decontaminated or sterilized. During the decontamination process, HP concentrations can reach levels of 2000 ppm or more, depending on the specific process and requirements, such as degree of sterile environment needed, type of microorganism to be eradicated, and the room contents and conditions.

Following decontamination, the enclosed area must be aerated to allow for re-use of the area. To be safe, the HP concentration normally needs to be reduced to a level of less than about 1 ppm. To return the facilities to use as quickly as possible, the aeration rate (HP removal rate, expressed in g/min) should be as fast as possible, especially in hospitals and surgical rooms, in order to avoid costly downtime. Here, even accelerating the aeration time by a few minutes can matter.

Using a catalyst to accelerate the decomposition of hydrogen peroxide into water and oxygen is well known in the chemical literature. Catalysts such as activated carbon, metal oxides, and rare earth metals are known to enhance the decomposition of HP. The catalysts are typically fashioned into catalytic converters—metal substrates coated with platinum, palladium, or other metal oxides or transition metals known to decompose HP. When catalytic converters are applied to the problem of removing residual hydrogen peroxide vapor sterilant from a decontaminated area, however, the flow configuration, catalyst selection, catalyst bed formulation, and other factors complicate their successful implementation. In particular, there tends to be a decreased efficiency of the catalysts at lower concentrations of the residual HP.

In U.S. Pat. No. 7,354,551, Mielnik et al, teach a two-step process for removal of hydrogen peroxide gas from a room during a decontamination process. In the first step, HP-laden air is forced by a pump through a catalytic converter and then exits the system. HP-laden air is recycled through the system until the concentration is reduced to a level of 1 ppm or less. In the second step, a dehumidifier is used to further reduce the HP concentration and return the room atmosphere to a safe level for re-occupancy. The problem with the Mielnik method is that, because of the kinetic limitation (high flow and low residence time), the first step can take hours to achieve, and further, two separate pieces of equipment are needed, a catalytic converter and then a dehumidifier, causing undue cost and complexity in the device.

A different approach is taught in U.S. Pat. No. 7,988,911 issued to Centanni et al. Centanni teaches a two-stage method to remove residual hydrogen peroxide by passing the HP-containing gas through a catalytic converter and then through a chemical reaction system, such as thiosulphate and iodide chemicals, to remove the last traces of HP. The two-stage system is complex and costly to manufacture, and requires the use of a disposable chemical cartridge, which creates unnecessary chemical waste and further increases the cost to operate the system.

Besides the two stage processes, the prior art does not address improved efficiency of aerator through-flow and catalyst surface area optimization. Thus, a rapid residual biocide removal method with a greatly enhanced efficiency (2-3 fold) is needed, preferably by optimizing air flow pattern, air transport rate, cleaned air discharge pattern, and the nature and configuration of the catalyst.

SUMMARY OF THE PRESENT INVENTION

The present development is an apparatus and method for improving the efficiency of an aerator which is used for removing residual biocide used for decontamination, sterilization, sanitation, or disinfection processes. The apparatus comprises an aerator assembly that controls the biocide-laden air flow and direction, and a high surface area catalyst panel. The catalyst panel efficiency is optimized by selection of the catalyst material and by designing a catalyst bed with optimum porosity and substrate configuration. The apparatus further comprises an inlet and an outlet configured such that cleaned gas is not allowed to immediately recirculate back into the apparatus and the discharged cleaned gas does not prematurely mix to cause undue dilution of the remaining biocide-laden gas in the room.

The method comprises utilizing the apparatus with optimized gas flow rates to maximize the residence time of the contaminated gas within the catalyst panel. Specifically, the air transport rates, the ratio of gas flow rate to the total catalyst active surface area ratio, momentum transfer, the residence time, the face velocity, and the effective catalyst area exposed to gas interaction including orientation are optimized in order to maximize the efficiency of the catalyst in decomposing the residual HP in a room. Further, the flow pattern of gas through the device is configured such that the catalyst efficiency is maximized and the need for additional flow patterns within the device is unnecessary, and significantly improves the aeration rate.

DETAILED DESCRIPTION OF THE INVENTION

Figure 1A:
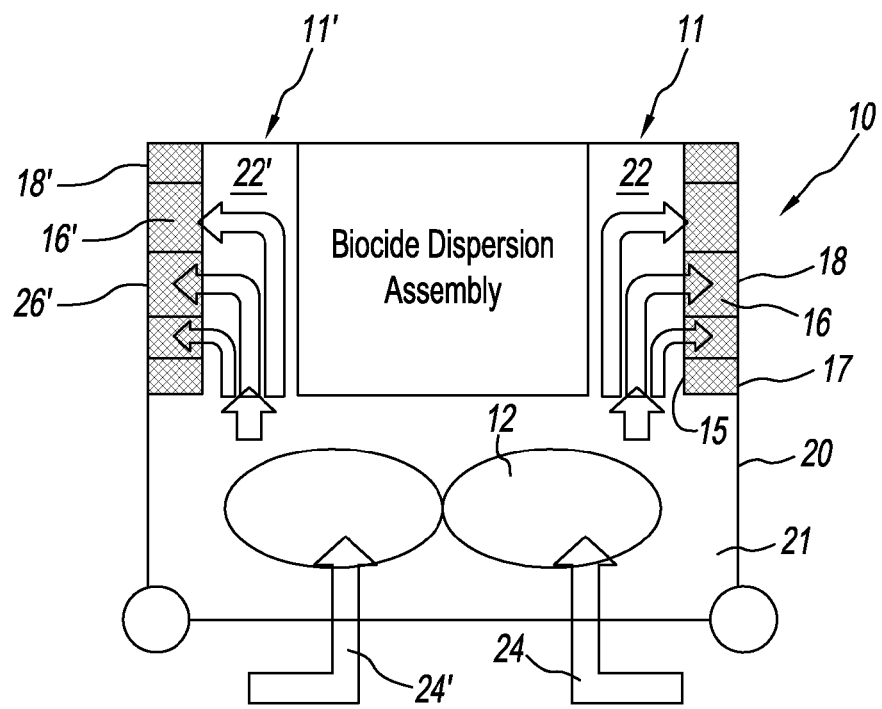
FIG. 1A is a schematic of a biocide reducing aeration system designed to produce an annular flow made in accordance with the present invention.

The following description is intended to provide the reader with a better understanding of the invention. The description is not intended to be limiting with respect to any element not otherwise limited within the claims.

For the purpose of this disclosure, the specified terms shall be defined as follows:

"Aeration rate" is the mass of biocide, for example hydrogen peroxide (HP), decomposed or removed from a decontamination area per minute (g/min) at given initial concentration ($g/m^3$) of injected biocide. The aeration rate depends on the injected mass density and room volume in addition to catalyst properties and air flow pattern. Aeration rate may increase with increasing injected mass.

"Flow to face area ratio or FFAR" is an abbreviated term referring to the ratio of gas or air flow rate, typically expressed as cubic feet per minute or CFM, divided by the total geometric, or active, surface area. The active surface area is the catalyst face area that directly faces air or gas flow for a given catalyst thickness. The ratio (FFAR) is expressed in terms of the velocity unit of feet per minute (ft/min) or meters per second (m/s). FFAR has an optimum range of 2-5 m/s, and is dependent of the nature and configuration of the catalyst panel. FFAR is a term defined for the aerator and is localized to aerator. This is calculated using the blower volumetric flow and total catalyst surface area. On the other hand, catalyst "face velocity" which has the similar physical significance as FFAR, is usually a measured quantity. However, it can be calculated too. Face velocity depends on the incident flow velocity, catalyst face area, honeycomb cell structure, and clearance/diameter.

"Flow direction in relation to catalyst panel" refers to whether the gas is being pushed through the catalyst or the gas is being pulled through the catalyst. How the gas passes through the catalyst affects aeration efficiency.

"Air transport rate or ATR" is the rate at which air is exchanged between the aerator and the room. The ATR is expressed in velocity terms of feet per minute or meters per second. The aerator efficiency is also influenced by the geometrical area of the catalyst and its properties. The aerator efficiency is also linked to ATR both by magnitude and direction.

The aeration rate or the time to reduce the biocide residue to a level acceptable to allow for space re-use is as important as the inactivation or decontamination process itself. Depending on the specific application, the time needed for an aerator to reduce the biocide concentration to the safe-entry level may become extremely valuable, for example in the case of hospital surgery rooms. The present development focusses on reducing the aeration time to the shortest possible extent while allowing for the biocide mass to reach the optimum level for the inactivation of the targeted biologic contaminants and material stability. Factors that affect aeration rate, or that improve aerator efficiency, include the catalyst bed substrate selection and configuration, the catalyst composition, catalyst cell density, the flow impingement on the catalyst surface, the residence time on the catalyst surface, and the configuration of the inlet and exit flow of the device.

Figure 2A:
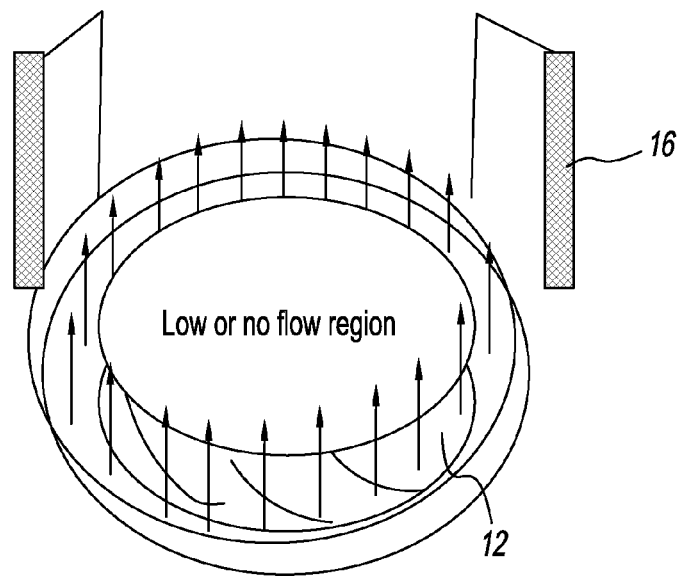
FIG. 2A is an illustration of the annular airflow pattern generated by the aerator of the aeration system of FIG. 1A as the biocide-laden air is pushed toward the catalyst panel.

The present development is an apparatus for removing a biocide vapor-laden gas remaining inside an enclosed room after the room has been subjected to an area decontamination process. As shown in FIG. 1A, the biocide vapor reducer or aeration system 10 comprises a housing 20 and at least one aerator 11, the aerator comprising at least one air moving device 12 and at least one catalyst panel 16, 16'. Biocide-laden gas or air is drawn into the interior of the housing 21 through an inlet or plenum 24, 24'. The air moving device 12 moves the air into a pre-treatment chamber 22, 22' or space within the housing 20 before the air enters the catalyst panel 16, 16'. After passing through the catalyst panel 16, the air is discharged through an outlet 26 back into the room. In the design of FIG. 1A, the selection of an impeller air moving device as the air moving device 12 results in an annular airflow leading to the catalyst panels 16, 16', as shown in FIG. 2A.

Figure 1B:
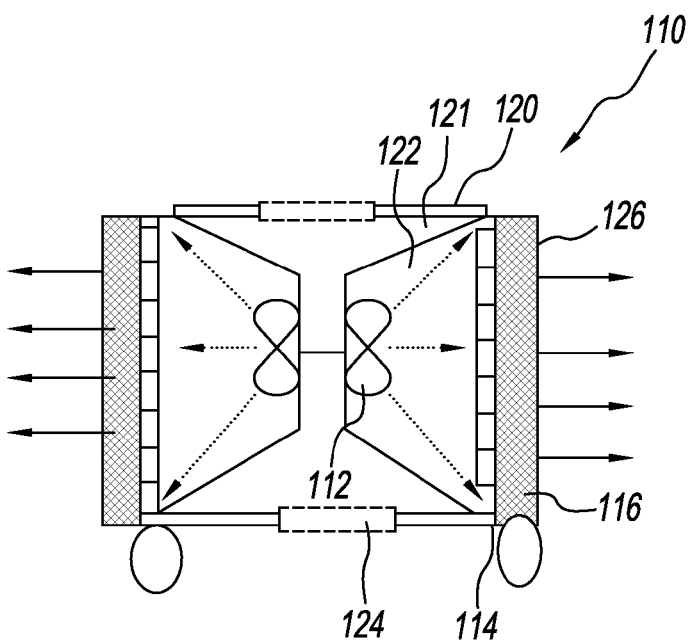
FIG. 1B is a schematic of a first alternative embodiment for a biocide reducing aeration system made in accordance with the present invention designed to produce a head-on flow and further showing a twin aerator option.
Figure 2B:
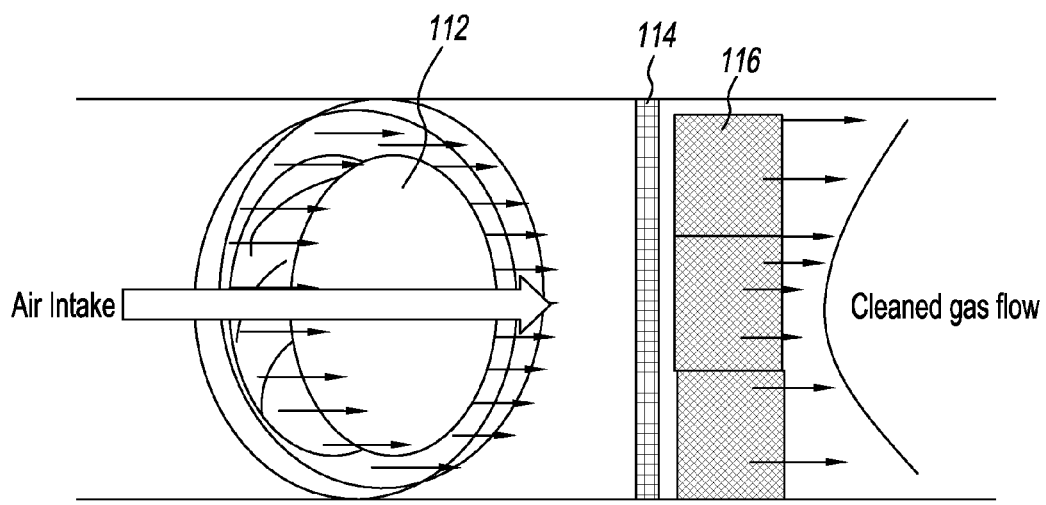
FIG. 2B is an illustration of the head-on airflow pattern generated by the aerator of the aeration system of FIG. 1B as biocide-laden air is pushed toward the catalyst panel and flows through a filter, then into the catalyst panel, and then as the air exits the catalyst panel.

In a first alternative embodiment, shown in FIG. 1B, the biocide vapor reducer or aeration system 110 comprises a housing 120 and at least one aerator 111, the aerator comprising at least one air moving device 112, and at least one catalyst panel 116. Biocide-laden gas or air is drawn into the interior of the housing 121 through an inlet or plenum 124. The air moving device 112 moves the air into a pre-treatment chamber 122 or space within the housing 120 before the air enters the catalyst panel 116. After passing through the catalyst panel 116, the air is discharged through an outlet 126 back into the room. In the design of FIG. 1B, the selection of a blower as the air moving device 112 results in head-on airflow leading to the catalyst panel 116, as shown in FIGS. 2B and 2C.

Optionally, at least one air filter may be positioned between the air moving device and the catalyst panel. If the optional air filter is included in the aerator 111, it is preferable to have the biocide-laden air pass through the filter before entering the catalyst panel. As shown in FIG. 2B, the filter 114 may be positioned between the air moving device 112 and the catalyst panel 116. Alternatively as shown in FIG. 2C, the filter 114 may be positioned before the air moving device 112 so the biocide-laden air is pulled through the filter 114 and then pushed by the air moving device 112 toward the catalyst panel 116. A second alternative embodiment is shown in FIG. 2D wherein the biocide-laden air is pulled through the filter 114, and is then pulled through the catalyst panel 116, before reaching the air moving device 112.

Figure 2C:
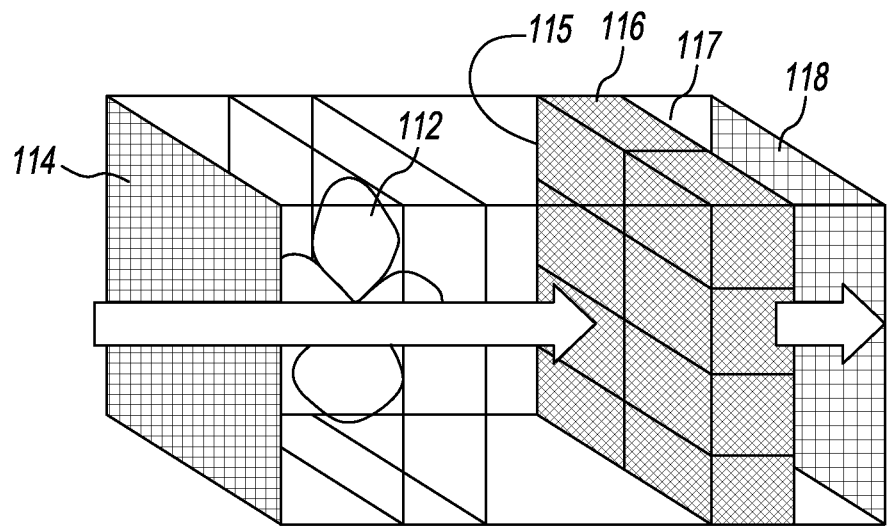
FIG. 2C is an illustration of a second alternative airflow pattern that is produced when the air moving device of the aerator is positioned to push a head-on airflow directly onto the face the catalyst panel, with the air then exiting the catalyst panel.
Figure 2D:
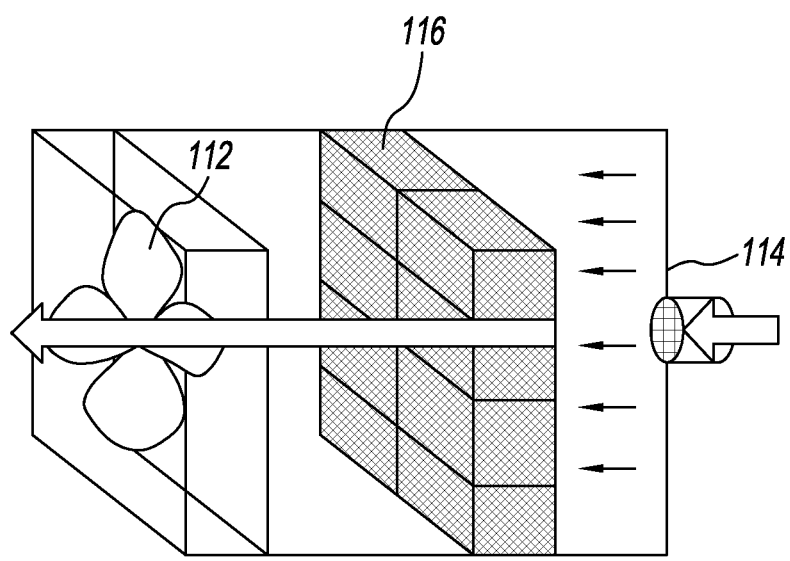
FIG. 2D is an illustration of the airflow pattern that is produced when the air moving device of the aerator is used to pull biocide-laden air through the catalyst panel before the air contacts the air moving device.
Figure 3:
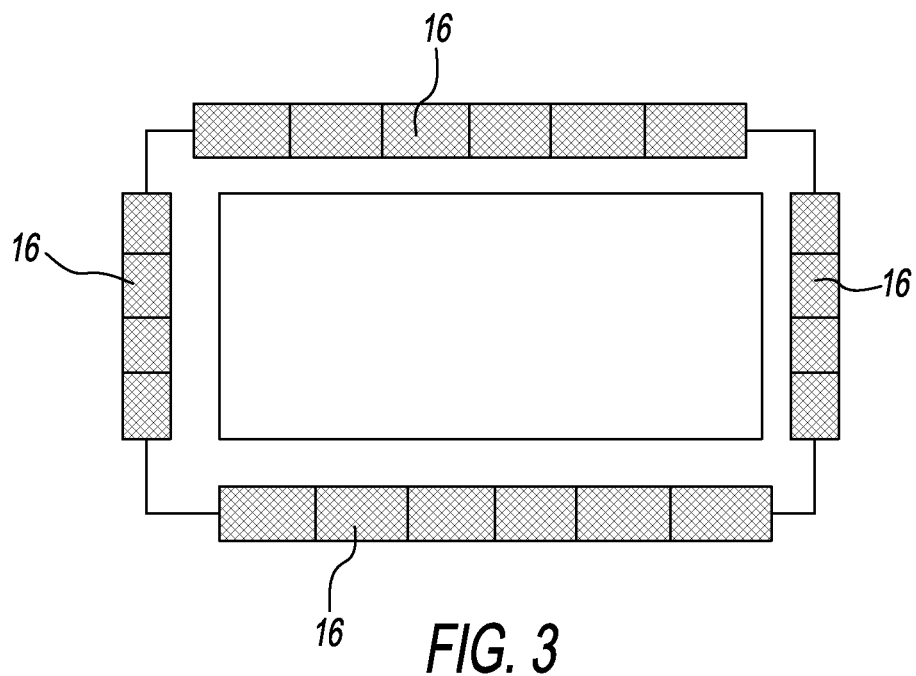
FIG. 3 is a top view of an exemplary orientation of a plurality of catalyst panels when used in a biocide-reducing aerator made in accordance with the present invention.
Figure 4A:
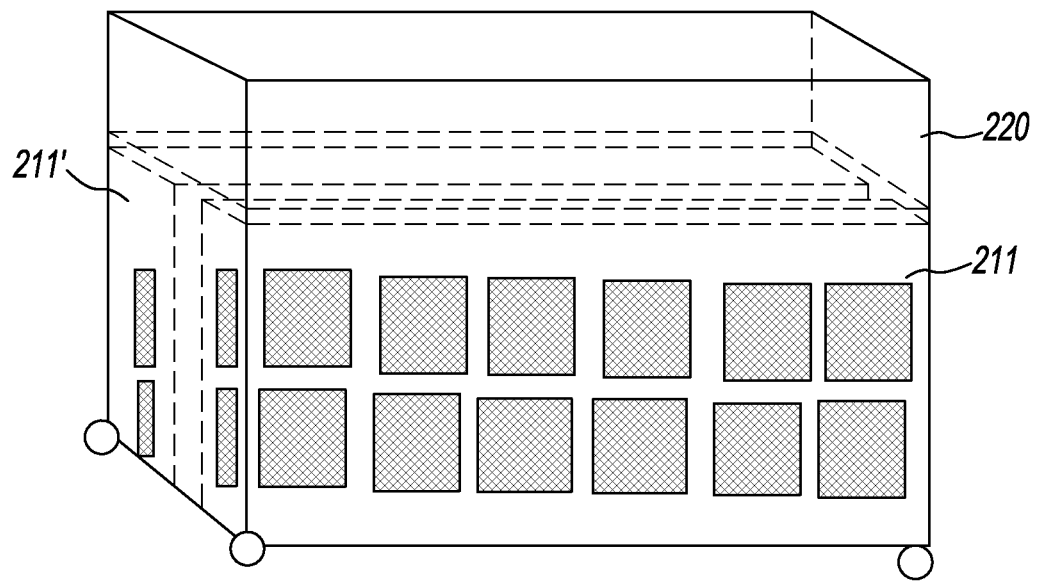
FIG. 4A is a perspective view of a biocide-reducing dual-aerator system made in accordance with the present invention.
Figure 4B:
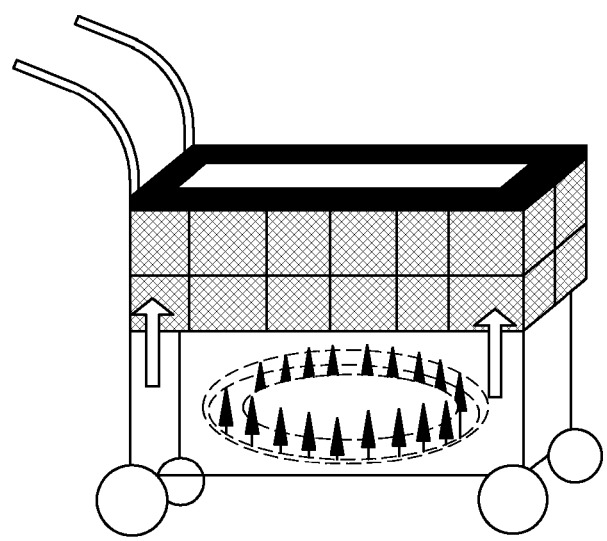
FIG. 4B is a perspective view of the biocide-reducing aerator of FIG. 1.
Figure 4C:
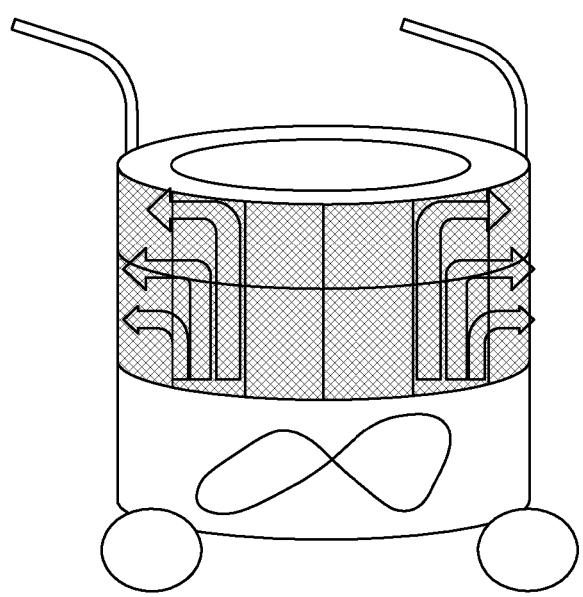
FIG. 4C is a perspective view of a first alternative embodiment of the annular flow biocide-reducing aerator made in accordance with the present invention; and, FIG. 5 is a top view of a biocide-reducing aerator made in accordance with the present invention with additional fans or blowers included to optimize air exchange between the aerator and the enclosed room.
Figure 5:
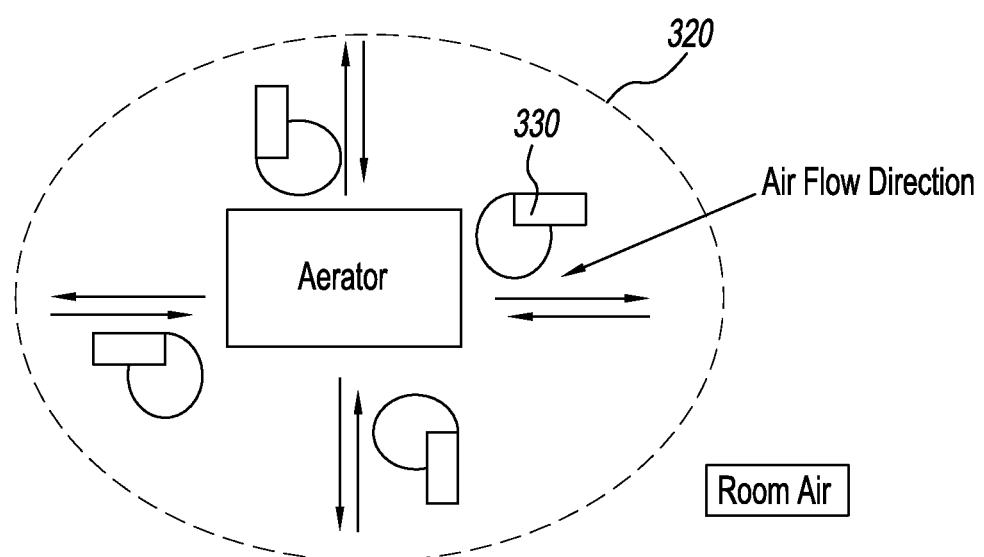

As shown in FIGS. 1A and 2C, the catalyst panel 16, 116 defines an interior surface 15, 115 and an exterior surface 17, 117. When mounted within the aeration system 10, 110, the interior surface 15, 115 faces the air moving device 12, 112, and the exterior surface 17, 117 is exposed to the biocide-laden space. To accommodate the catalyst panel 16, 116, the housing 20, 120 must include apertures (not shown) or voids of sufficient dimension to snuggly contain the catalyst panel 16, 116 without allowing for leakage of biocide-laden air from within the housing before the air has been in intimate contact with the catalyst panel 16, 116. Because the exterior surface 17, 117 of the catalyst panel 16, 116 is exposed, an optional grid 18, 118 may be placed adjacent to the surface 17, 117 to protect the catalyst panel 16, 116 from physical damage.

To maximize efficiency, it is important to minimize the amount of biocide-reduced air that is recycled through the aerator 11, 111. Thus, it is preferable that the aerator components are arranged within the unit such that the inlet 24, 124 and outlet 26, 126 of the device avoids allowing the cleaned air to immediately recirculate back into the inlet. With this configuration, the expelled clean air slowly displaces the biocide-laden air in the room without undue mixing and reduces the volume of air that must flow through the aerator to achieve the target biocide concentration.

The air moving device 12, 112 may be any device that can move gas or air at a rate of from about 500 CFM to about 5000 CFM. In a preferred embodiment, the air moving device 12 is a motorized impeller fan with a high volume airflow. Ideally, the air moving device 12, 112 may be configured to either pull or to push the biocide-laden air through the catalyst panel 16, 116.

The catalyst panel 16, 116 defines an active surface area, or the surface area directly exposed to the biocide-laden air. For the purpose of illustration only, assuming the interior surface of the catalyst panel has a square geometry with a 6 inch length and a 6 inch height, and that the catalyst panel is mounted within the aerator such that the interior surface is directly exposed to the biocide-laden air, the active surface area would be calculated to be 0.25 $ft^2$ (0.5 ft×0.5 ft). To maximize efficiency, the active surface area is preferably between about 2 $ft^2$ to about 12 $ft^2$. More preferably, the active surface area is between about 3 $ft^2$ to about 8 $ft^2$. Most preferably, the active surface area is between about 3 $ft^2$ to about 5 $ft^2$. In order to achieve the desired active surface area, it is anticipated that the dimensions of a single catalyst panel may be varied, or a plurality of catalyst panels may be aggregated into an array in an aerator, such as shown in FIG. 3, to increase the active surface area and wherein the active surface area is equal to the sum of the individual catalyst panel active surface areas.

The catalyst panel thickness will affect airflow velocity and the desired residence time of the gas on the catalyst surface. Preferably, the catalyst panel will have a thickness of from about 0.5 inches to about 6 inches. More preferably, the catalyst panel will have a thickness of from about 1 inch to about 4 inches. Most preferably, the catalyst panel will have a thickness of about 2 inches.

The selection of the catalyst substrate is a key factor in maximizing the aeration efficiency. The catalyst substrate may be ceramic, porcelain, cordierite, metal, or combinations thereof. The catalyst substrate may have a variety of shapes as are known in the art. In a preferred embodiment, the substrate is a ceramic honeycomb.

A metal catalyst is carried on the substrate. The metal catalyst is selected from precious metals, noble metals, transition metals, metal oxides, or combinations thereof. Preferably, the metals or metal oxides for the catalyst panel comprise platinum, palladium, copper, rare earth metals, platinum oxide, palladium oxide, manganese dioxide, copper oxide, rare earth metal oxides, or combinations thereof. More preferably, the metals or metal oxides for the catalyst panel comprise palladium.

The metal catalyst may be deposited on the substrate using any technique known in the art. In a preferred embodiment, a nano-coating (nanomaterial) is used. Nanocoated catalysts show significant efficiency enhancement at a much lower catalyst concentration. One common technique is to wash-coat the substrate with a metal-containing solution until the substrate has the desired surface concentration of metal. In the present development, the metal surface concentration is preferably between about 2 g/$ft^3$ and 60 g/$ft^3$, more preferably between about 7.5 g/$ft^3$ and 40 g/$ft^3$, and most preferably between about 12 g/$ft^3$ and 18 g/$ft^3$.

The honeycomb substrate structure may have hexagonal, circle, square or other sub-geometry cell structures, as are known in the art. Further, the honeycomb substrate structure preferably has a cell concentration of from about 200 cells per square inch of face area to about 600 cells per square inch of face area. More preferably, the honeycomb substrate structure has a cell concentration of from about 200 cells per square inch of face area to about 450 cells per square inch of face area. Most preferably, the honeycomb substrate structure has a cell concentration of from about 300 cells per square inch of face area to about 400 cells per square inch of face area.

The volumetric airflow rate through the device is optimized with respect to the depth of the catalyst plate, the concentration of catalyst, the flow to face area ratio (FFAR) and the air transport rate in the room. The FFAR is preferably from 1.5 msec to 8 msec, and more preferably is from 4 msec to 7 msec, and most preferably is approximately 3 msec.

It is desirable to maximize the airflow at the face of the catalyst panel. In the aeration system of the present development, the flow configuration increases the aeration rate by enhancing the gas-surface reaction rates via optimizing the flow impingement with honeycomb catalyst structure cell walls. The velocity profiles are demonstrated to be unique in increasing the decomposition rates with hydrogen peroxide vapors at the monolith walls because of the solid-gas reaction rates.

Depending on selection of the type of air moving device 12, 112, the biocide-laden gas can flow toward the catalyst panel 16, 116 head-on, perpendicular, or in an annular pattern. The flow vector has a decisive influence on the performance of the catalytic reactions and, hence, the aerator performance. As shown in FIGS. 1A and 2A, if the air moving device 12 is an impeller fan, the airflow is maximized at the circumference of the fan's range forcing the biocide-laden air toward the face of the catalyst panel 16 in an annular pattern. Alternatively, FIGS. 1B, 2B and 2C utilize a blower as the air moving device 112 and deliver the gas in a head-on direction.

Further, the biocide-laden gas can be either pushed or pulled through the catalyst panel. When gas is pushed through the catalyst panel 16, 116, as shown in FIGS. 2A, 2B and 2C, the velocity-through-catalyst flow follows the incident velocity pattern generated by the air moving device 12, 112. However, when the gas is pulled through the catalyst panel, as shown in FIG. 2D, relying on a vacuum principle, the velocity is generally uniform through the catalyst. To maximize efficiency, the catalyst panel 16, 116 is preferably positioned such that the entire active surface area is impacted by the air flow.

The interaction of the biocide-laden air with the catalyst panel 16, 116 causes the biocide to decompose. The now-cleaned air along with the decomposition products, e.g. oxygen and water vapor produced from hydrogen peroxide, are discharged directly out of the catalyst panel 16, 116 and back into the enclosed room.

One measure of efficiency in the aerator of the present development is the ratio of airflow to the catalyst active surface area (FFAR), or the incident velocity on the catalyst panel, expressed as CFM/CAT which can be converted to m/s. The aeration rate is low at high FFAR such as 8 m/s and is also low at low FFAR such as around 1.5 m/s. The optimum aeration rate is observed to occur around 3 m/s. This is a calculated FFAR number. For example, if the blower operates at 4000 CFM and there are 28 catalyst panels and each catalyst panel has a 36 sq. inch (6"×6") active surface area, the calculated value for FFAR is 2.9 m/s. The measured velocity through the catalyst is an experimental quantity, and is generally referred as "face velocity (m/s)". The face velocity and FFAR will follow the similar trend but the numerical values will differ.

As shown in FIGS. 1B and 4A, more than one aerator 111', 211 may be mounted within a single housing 120, 220. Each aerator would function as an individual unit to reduce the biocide concentration from the air, but it is anticipated that the functioning of the units could be coordinated so they would operate in tandem to accomplish the desired biocide reduction. Further, the housing may have a variety of configurations, such as shown in FIGS. 4A, 4B, and 4C while still allowing the aerators to function as intended.

EXAMPLES

The following examples are presented for illustrative purposes only and are not intended to limit the scope of the invention.

Example 1

An aeration system having a twin aerator assembly, or a first aerator and an essentially identical second aerator, similar to the design shown in FIG. 1B, comprises a housing having an air intake plenum on the base side; the air moving devices are blowers, and two blowers are mounted within the housing, each blower having a volumetric flow of 1300 CFM; two air filters are mounted downstream of the air moving devices; two catalyst panels each comprising a ceramic honeycomb substrate with 400 cells per square inch washcoated with palladium to deliver a palladium concentration of 15 $g/ft^2$ wherein each catalyst panel has dimensions of 6 inches (length)×6 inches (height)×2 inches (thickness); and two grids are mounted within the housing, one each providing protective cover for the catalyst panels. The blowers are controlled to push HP-laden air through the catalysts panels. For the first aerator, the average face velocity through the catalyst is about 5 m/s, the HP mass injected is about 25 g, the aeration time to 0.9 PPM HP concentration is about 25 minutes, and the aeration rate is calculated to be 1.0 g/min. For the second aerator, the average face velocity through the catalyst is about 5 m/s, the HP mass injected is about 27 g, the aeration time to 0.9 PPM HP concentration is about 25 minutes, and the aeration rate is calculated to be 1.1 g/min. When considered in combination, the average face velocity through the catalysts is about 5 m/s, the HP mass injected is about 28 g, the aeration time to 0.9 PPM HP concentration is about 14 minutes, and the aeration rate is calculated to be 2.0 g/min.

Example 2

An aeration system having an annular airflow aerator assembly, similar to the device shown in FIG. 1A, comprises a housing having an air intake plenum on the base side; the air moving device is a motorized impeller fan and one fan is mounted within the housing, the fan having a volumetric flow of 4000 CFM; and, twenty-eight catalyst panels, each comprising a ceramic honeycomb substrate with 400 cells per square inch washcoated with palladium to deliver a palladium concentration of 15 $g/ft^2$ wherein each catalyst panel has dimensions of 6 inches (length)×6 inches (height)×2 inches (thickness) for a total catalyst face area of 7 $ft^2$. The fan is controlled to push air through the catalyst panels. The average face velocity through the catalyst is about 6 m/s, the biocide is 27% by weight hydrogen peroxide solution injected into an enclosed space having a volume of 36 $m^3$ to deliver a mass of HP of about 25 g (this results in a mass concentration in the space of about 0.7 $g/m^3$), the aeration time to 0.9 PPM HP concentration is about 9 minutes, and the aeration rate is calculated to be 2.8 g/min.

Example 3

Using the same system as in Example 2 except changing the 27% HP solution to a 35% HP solution, the aeration rate varied from 2.5-3.8 g/min.

Example 4

Using the same system as in Example 2, except changing the fan control such that the fan pulls air through the catalyst panels, the air flow rate per unit of catalyst surface area is 2.9 m/s, the measured average velocity through the catalyst is 4.0 m/s, the aeration time to 0.9 PPM HP concentration is about 23 minutes, and the aeration rate is calculated to be 1.0 g/min.

As demonstrated by comparing Example 2 to Example 4, whether biocide-laden air is pushed through the catalyst panel or pulled through the catalyst panel can significantly affect the efficiency of the biocide reduction.

To this point, it has been assumed that only fans or blowers associated with the aerators are incorporated into each biocide reducing aeration system. Although, the air flow from the aerator into the room and vice versa are coupled (linked), they can be decoupled to some extent by adding additional fans. As shown in FIG. 5, optionally one or more exchange fans or blowers 330 may be mounted within the system housing 320 but external to the aerator 311. Functionally, these are auxiliary or booster fans aiding air exchange without affecting the main blower delivering air to catalyst panels. These exchange fans 330 optimize local flow conditions and enhance the air exchange rate. That is, they assist with moving treated or cleaned air back into the enclosed room by accelerating the velocity and/or changing the air flow pattern of the air that is external to the system but within the enclosed room. The local airflow inside the device defines FFAR and the residence time which in turn links to the air transport rate. This will not alter the optimized FFAR, and residence time locally accomplished for the device.

It is intended that that biocide-reducing aeration systems described herein can be used to remove biocide-laden air from a room or space after the room or space has been decontaminated. This can be accomplished by providing one of the biocide-reducing aeration systems described herein, drawing biocide-laden air from the room into the biocide reduction system through an inlet port on the system, forcing the biocide-laden air through the catalyst panel to produce cleaned air; and discharging the cleaned air from said biocide reduction system and back into the room, wherein the site of discharge is sufficiently separated from the inlet port that the cleaned air can mix with the biocide-laden air in the room. In a preferred embodiment, the biocide-reducing aeration system comprises a metal catalyst carried on a substrate and having an active surface area between about 2 $ft^2$ to about 12 $ft^2$, wherein a face area flow ratio is defined as air flow rate divided by the active surface area and the face area flow ratio is from 1.5 meters/sec to 8 meters/sec. In a more preferred embodiment, the biocide-reducing aeration system comprises a catalyst panel comprising palladium at a metal concentration between about 12 g/$ft^3$ and 18 g/$ft^3$ on a ceramic honeycomb having a cell concentration of from about 300 cells per square inch of face area to about 400 cells per square inch of face area. The method may be used to treat biocide-laden air, and in particular, air wherein the biocide is hydrogen peroxide, ozone, alcohol, biocidal organic compounds and their mixtures, peracetic acid, vinegar, organic acids, or any chemical agents that can inactivate or kill harmful microorganisms.

Specific dimensions relevant to the biocide reduction aeration device are provided herein for the purpose of demonstrating the invention, but these dimensions are not intended to limit the scope of the invention. It is understood that one skilled in the art may make alterations to the embodiments shown and described herein without departing from the scope of the invention. For example, it is anticipated that the catalyst panels may have a variety of geometric designs which would still allow for biocide reduction from an enclosed area.

What is claimed is:

1. A biocide reduction system for removing biocide-laden air from a room or space after the room or space has been decontaminated, said biocide reduction system comprising:
 a. at least one air moving device;
 b. at least one catalyst panel comprising a metal catalyst carried on a substrate, said catalyst panel defining an interior surface and an exterior surface, and a total active surface area between about 0.25 $ft^2$ to about 12 $ft^2$; and,
 c. a housing, having at least one inlet and having at least one aperture of sufficient dimension to accommodate said catalyst panel,
 wherein said air moving device is fixedly positioned within said housing, and said catalyst panel is secured within the aperture of said housing such that the interior surface of said catalyst panel faces said air moving device and the exterior surface is exposed to the biocide-laden space, and wherein the exterior surface further defines an outlet for said biocide reduction system said outlet being physically separated from said inlet, and wherein a face area flow ratio is defined as air flow rate divided by the active surface area and the face area flow ratio is from 1.5 meters/sec to 8 meters/sec.

2. The biocide reduction system of claim 1 wherein the air moving device can move air at a rate of from about 500 CFM to about 5000 CFM.

3. The biocide reduction system of claim 2 wherein the air moving device creates an annular airflow.

4. The biocide reduction system of claim 2 wherein the air moving device creates a head-on airflow.

5. The biocide reduction system of claim 1 further comprising at least one air filter.

6. The biocide reduction system of claim 5 wherein said air filter is positioned between said air moving device and said catalyst panel such that the alignment of components is said air moving device, then said air filter, and then said catalyst panel.

7. The biocide reduction system of claim 5 wherein said air filter is positioned relative to said air filter and said catalyst panel such that the alignment of components is said air filter, then said air moving device, and then said catalyst panel.

8. The biocide reduction system of claim 5 wherein said air filter is positioned relative to said air filter and said catalyst panel such that the alignment of components is said air moving device, then said catalyst panel, and then said air filter.

9. The biocide reduction system of claim 1 further comprising a grid to protect said catalyst panel, said grid positioned adjacent to the exterior surface of said catalyst panel.

10. The biocide reduction system of claim 1 wherein said catalyst panel has an active surface area between about 3 $ft^2$ to about 8 $ft^2$.

11. The biocide reduction system of claim 10 wherein said catalyst panel has an active surface area between about 3 $ft^2$ to about 5 $ft^2$.

12. The biocide reduction system of claim 1 wherein said catalyst panel defines a thickness and the thickness is from about 0.5 inches to about 6 inches.

13. The biocide reduction system of claim 1 wherein said catalyst panel comprises a substrate selected from ceramic, porcelain, cordierite, or metal, or combinations thereof.

14. The biocide reduction system of claim 1 wherein said metal catalyst is selected from platinum, palladium, copper, rare earth metals, platinum oxide, palladium oxide, manganese dioxide, copper oxide, rare earth metal oxides, or combinations thereof.

15. The biocide reduction system of claim 14 wherein said metal catalyst has a metal concentration between about 2 g/$ft^3$ and 60 g/$ft^3$.

16. The biocide reduction system of claim 14 wherein said metal catalyst has a metal concentration between about 7.5 g/$ft^3$ and 40 g/$ft^3$.

17. The biocide reduction system of claim 14 wherein said metal catalyst has a metal concentration between about 12 g/$ft^3$ and 18 g/$ft^3$.

18. The biocide reduction system of claim 13 wherein said catalyst panel substrate is a ceramic honeycomb having a cell concentration of from about 200 cells per square inch of face area to about 600 cells per square inch of face area.

19. The biocide reduction system of claim 18 wherein said ceramic honeycomb has a cell concentration of from about 200 cells per square inch of face area to about 450 cells per square inch of face area.

20. The biocide reduction system of claim 18 wherein said ceramic honeycomb has a cell concentration of from about 300 cells per square inch of face area to about 400 cells per square inch of face area.

21. The biocide reduction system of claim 1 wherein the face area flow ratio is from 4 m/sec to 7 m/sec.

22. The biocide reduction system of claim 1 wherein nanocoating technology is used to enhance the catalyst activity at a much lower catalyst concentration.

23. The biocide reduction system of claim 1 wherein said air moving device functions to push air through said catalyst panel.

24. The biocide reduction system of claim 1 wherein said air moving device functions to pull air through said catalyst panel.

25. The biocide reduction system of claim 1 comprising two air moving devices operating in tandem.

26. The biocide reduction system of claim 1 where additional or axillary fans are placed adjacent to the catalyst panels.

27. A method for removing biocide-laden air from a room or space after the room or space has been decontaminated, said method comprising:
   a. providing a biocide reduction system comprising at least one air moving device and at least one catalyst panel comprising a metal catalyst carried on a substrate and having an active surface area between about 0.25 $ft^2$ to about 12 $ft^2$, wherein a face area flow ratio is defined as air flow rate divided by the active surface area and the face area flow ratio is from 1.5 meters/sec to 8 meters/sec;
   b. drawing biocide-laden air from the room into the biocide reduction system through an inlet port on the system;
   c. forcing the biocide-laden air through said catalyst panel to produce cleaned air; and,
   d. discharging the cleaned air from said biocide reduction system and back into the room, wherein the site of discharge is sufficiently separated from the inlet port that the cleaned air can mix with the biocide-laden air in the room.

28. The method of claim 25 wherein said catalyst panel comprises palladium at a metal concentration between about 12 $g/ft^3$ and 18 $g/ft^3$ on a ceramic honeycomb having a cell concentration of from about 300 cells per square inch of face area to about 400 cells per square inch of face area.

29. The method of claim 27 wherein the biocide is hydrogen peroxide, ozone, alcohol, organic compounds and their mixtures, peracetic acid, vinegar, organic acids, or any chemical agents that can inactivate or kill harmful microorganisms.

* * * * *